US00PP23955P3

(12) United States Plant Patent
Meilland

(10) Patent No.: US PP23,955 P3
(45) Date of Patent: Oct. 8, 2013

(54) HYBRID TEA ROSE PLANT NAMED 'MEICALANQ'

(50) Latin Name: *Rosa hybrida*
Varietal Denomination: Meicalanq

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 369 days.

(21) Appl. No.: 13/064,223

(22) Filed: Mar. 11, 2011

(65) Prior Publication Data

US 2012/0096608 P1 Apr. 19, 2012

(51) Int. Cl.
*A01H 5/00* (2006.01)

(52) U.S. Cl.
USPC ..... Plt./133

(58) Field of Classification Search
USPC ..... Plt./133
See application file for complete search history.

(56) References Cited

PUBLICATIONS

Anonymous. 'MEIcalanq' Rose. HelpMeFind. available at: http://www.helpmefind.com/rose/1.php?1-21.175870 accessed May 3, 2013.*

PLUTO UPOV ROM Database, Citations for 'Meicalanq' Accessed May 6, 2013.*

* cited by examiner

*Primary Examiner* — Wendy C Haas
(74) *Attorney, Agent, or Firm* — Buchanan Ingersoll & Rooney PC

(57) ABSTRACT

A new and distinct Hybrid Tea rose plant is provided that commonly commences blooming early in the season and forms abundantly and substantially continuously attractive pure white very double blossoms which display a very strong fragrance. The growth habit is semi-erect, and very strong vegetation is formed. The vegetation is decorative and very dense and bears a glossy aspect on the upper surface. No particular disease problem has been observed. The plant is particularly well suited for providing attractive ornamentation in parks and gardens.

1 Drawing Sheet

Figures 1, 2, 3, 4, 5, 6, 7, 8, 9, 10, 11, 12, 13, 14, 15, 16, 17:
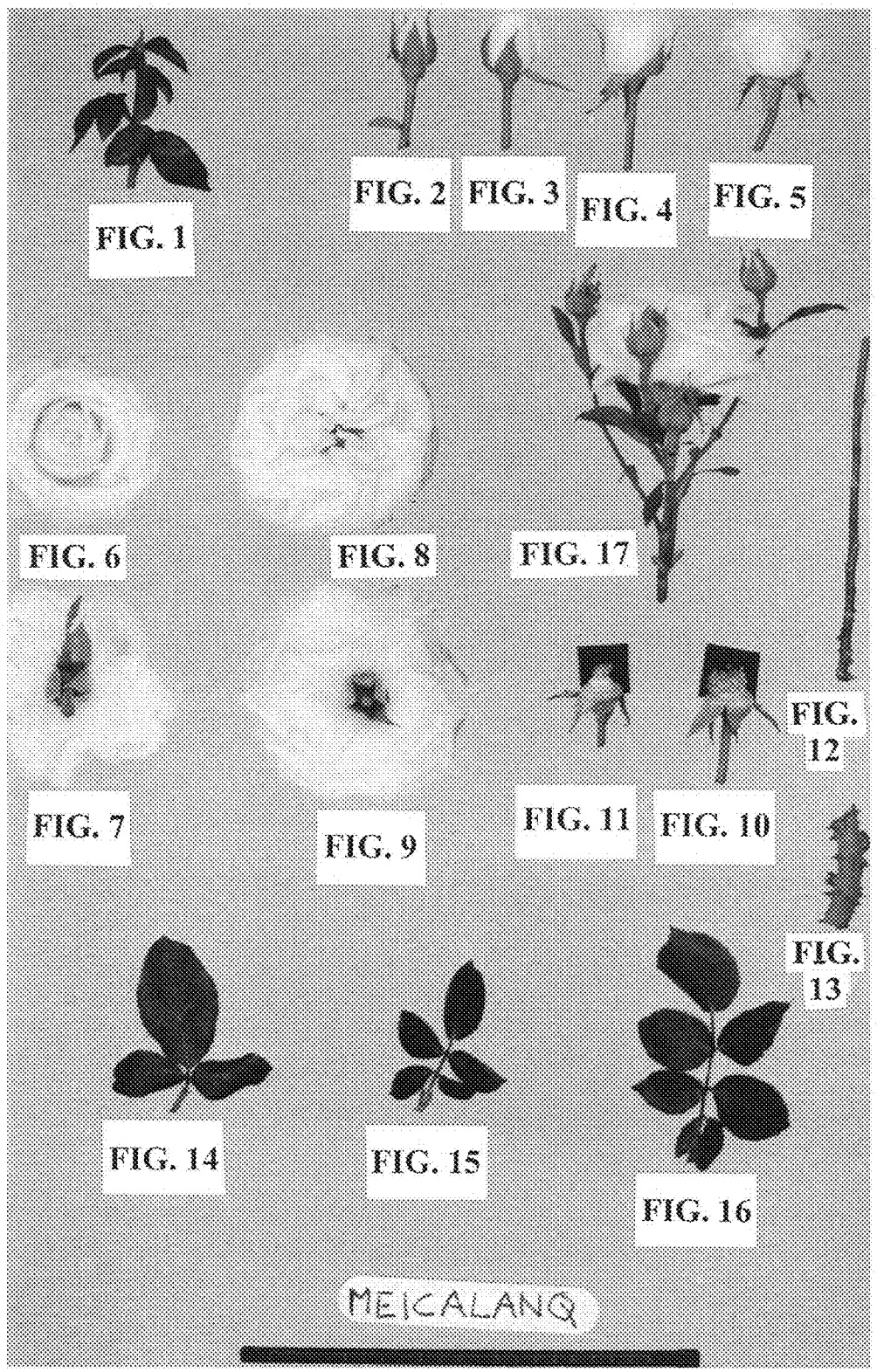

Botanical/commercial classification: *Rosa hybrida*/Hybrid Tea Rose Plant.

Varietal denomination: cv. Meicalanq.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Typhoon' variety (non-patented in the United States) and 'Meivildo' variety (U.S. Plant Pat. No. 6,895). The male parent (i.e., the pollen parent) was the 'Meimagarmic' variety (U.S. Plant Pat. No. 5,067).

The parentage of the new variety can be summarized as follows:

('Typhoon'×'Meivildo')×'Meimagarmic'.

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays a semi-erect growth habit with strong vegetation, (b) forms in abundance on a substantially continuous basis attractive pure white very double blossoms which display a very strong fragrance, (c) exhibits decorative very dense glossy dark green foliage, and (d) is particularly well suited for providing attractive ornamentation in parks and gardens.

The blooming tends to commence early in the season, during observations to date.

The new variety well meets the needs of the horticultural industry and can be grown to advantage where attractive ornamentation is to be provided.

The new variety can be readily distinguished from its ancestors. For instance, the blossom coloration is considerably different from that of the 'Typhoon' and 'Meivildo' varieties. More specifically, the 'Typhoon' variety forms yellow blossoms and the 'Meivildo' variety forms neyron pink blossoms. Also, the blossoms of the 'Meimagarmic' variety are of a dissimilar empire yellow coloration and are suffused and edged with an amaranth red flush.

The new variety has been found to undergo asexual propagation in France by a number of routes, including budding, grafting, and the use of cuttings. Asexual propagation by the above-mentioned techniques at Le Gannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meicalanq'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during October while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud at the opening of the sepals;

FIG. 3—illustrates a specimen of a floral bud wherein the sepals are fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—upper surface;

FIG. 16—illustrates a specimen of a leaf with seven leaflets—plan view—upper surface; and FIG. 17—illustrates a cluster of buds.

DETAILED DESCRIPTION

The chart used in the identification of the colors is that of The Royal Horticultural Society (R.H.S. Colour Chart). The description is based on the observation of two-year-old plants during October which were budded on *Rosa froebelli* understock and growing outdoors at Le Cannet des Maures, Var, France.

Class: Hybrid Tea.

Plant:

*Growth habit.*—Semi-erect.

Branches:

*Color.*—Young stems: near Green Group 138B. Adult wood: near Green Group 138B.

*Thorns.*—On young stems: Small prickles: Configuration: with an obovate base. Quantity: approximately 2 on average on a stem length of 10 cm. Length: approximately 0.2 cm on average. Color: near Greyed-Orange Group 165A. Long prickles: Configuration: with an obovate base. Quantity: approximately 15 on average on a stem length of 10 cm. Length: approximately 0.6 cm on average. Color: near Greyed-Orange Group 165A. On adult stems: Small prickles: Configuration: commonly none present. Long prickles: Configuration: elongated and curved downwards on the upper surface and concave on the under surface. Quantity: approximately 12 on average on a stem length of 10 cm. Length: approximately 0.5 cm on average. Color: near Yellow-Green Group 148D.

Leaves:

*Stipules.*—Adnate, pectinate, rather broad, approximately 1.2 cm in length on average, approximately 0.7 cm in width on average, near Yellow-Green Group 147C on the upper surface, and near Yellow-Green Group 147B on the under surface.

*Petioles.*—Upper surface: near Yellow-Green Group 147C in coloration. Under surface: near Yellow-Green Group 147B in coloration. Length: approximately 1.8 cm on average for the terminal leaflet. Texture: slightly glandular on the upper surface, and with small prickles on the under surface.

*Rachis.*—Upper surface: near Yellow-Green Group 146C in coloration. Under surface: near Yellow-Green Group 147B in coloration.

*Leaflets.*—Number: 3, 5 and 7 (most often). Shape: generally oval with an acuminate tip and a rounded base. Size: the terminal leaflets commonly are approximately 7 cm in length on average and approximately 4.6 cm in width on average. Serration: small and single (as illustrated). Texture: physically firm and leathery. Color (young foliage): Upper surface: near Green Group 137B. Under surface: near Green Group 139C. Color (adult foliage): Upper surface: near Green Group 139A. Under surface: near Yellow-Green Group 146B.

Inflorescence:

*Number of flowers.*—Commonly approximately 1 blossom per stem.

*Peduncle.*—Smooth, approximately 5 to 7 cm in length on average, approximately 0.4 cm in diameter on average, and near Yellow-Green Group 146C in coloration.

*Sepals.*—Upper surface: tomentose and near Green Group 138C in coloration. Under surface: smooth and near Green Group 138A and 138B in coloration. Shape: longish and broad, and somewhat upright at the base. Size: approximately 3 cm in length on average, and approximately 1.1 cm in width at the widest point on average.

*Buds.*—Shape: substantially conical and ovoid. Size: medium. Length: approximately 1.5 cm on average. Width: approximately 1 cm at the widest point on average. Color as calyx breaks: Upper surface: near White Group 155A. Under surface: near White Group 155A.

*Flower.*—Shape: cup-shaped. Diameter: approximately 13 to 14 cm on average. Color (in the course of opening): Upper surface: near White Group 155A. Under surface: near White Group 155A. Color (open flower): Upper side: near White Group 155A. Under side: near White Group 155A. Fragrance: very strong. Petal number: approximately 50 to 55 on average under normal growing conditions. Petal shape: with a substantially rounded tip and an obtuse base. Petal texture: leathery and somewhat firm. Petal length: approximately 3 cm on average. Petal width: approximately 1.1 cm on average. Petal arrangement: imbricated, and without petaloids. Petal drop: good with the petals commonly detaching cleanly before drying. Stamen number: approximately 48 on average. Anthers: regularly arranged around the styles, approximately 0.2 cm in size on average, and near Yellow-Orange Group 15D in coloration. Filaments: approximately 0.5 cm in length on average, and near Yellow Group 11D in coloration. Pollen: near Yellow-Orange Group 16B in coloration. Pistils: approximately 73 on average. Stigmas: approximately 0.2 cm in size on average, and near Yellow Group 13D in coloration. Styles: approximately 0.4 cm in length on average, and near Yellow Group 11D in coloration. Receptacle: smooth, funnel-shaped in longitudinal section, approximately 0.6 cm in length on average, approximately 0.5 cm in width on average at the widest point, and near Yellow-Green Group 146C in coloration.

Development:

*Vegetation.*—Very strong.

*Blooming.*—Early season, very abundant and substantially continuous.

*Tolerance to diseases.*—Good, with no particular susceptibility to common diseases having been encountered during observations to date.

The new 'Meicalanq' variety has not been observed under all possible environmental conditions to date. Accordingly, it is possible that the phenotypic expression may vary somewhat with changes in light intensity and duration, cultural practices, and other environmental conditions.

I claim:

1. A new and distinct Hybrid Tea rose plant characterized by the following characteristics:

(a) displays a semi-erect growth habit with strong vegetation, (b) forms in abundance on a substantially continuous basis attractive pure white very double blossoms which display a very strong fragrance, (c) exhibits decorative very dense glossy dark green foliage, and (d) is particularly well suited for providing attractive ornamentation in parks and gardens;

substantially as shown and described.

* * * * *

MEICALANQ